United States Patent
Lin

(10) Patent No.: US 7,101,177 B2
(45) Date of Patent: Sep. 5, 2006

(54) SCREW DEVICE FOR ORTHODONTIC TREATMENT

(76) Inventor: Cheng-Yi Lin, No. 190-1, Sec. 1, WenHua Rd., Banchiau, Taipei County (TW)

( * ) Notice: Subject to any disclaimer, the term of this patent is extended or adjusted under 35 U.S.C. 154(b) by 0 days.

(21) Appl. No.: 11/147,329

(22) Filed: Jun. 8, 2005

(65) Prior Publication Data

US 2005/0227197 A1 Oct. 13, 2005

Related U.S. Application Data

(63) Continuation-in-part of application No. 10/885,580, filed on Jul. 8, 2004, which is a continuation-in-part of application No. 10/732,292, filed on Dec. 11, 2003, which is a continuation-in-part of application No. 10/359,577, filed on Feb. 7, 2003, now Pat. No. 6,722,879, which is a continuation-in-part of application No. 10/211,037, filed on Aug. 5, 2002, now Pat. No. 6,726,475.

(51) Int. Cl.
*A61C 3/00* (2006.01)
*A61C 8/00* (2006.01)
(52) U.S. Cl. ........................................ 433/18; 433/174
(58) Field of Classification Search ................ 433/18, 433/172, 173, 174, 175, 176
See application file for complete search history.

(56) References Cited

U.S. PATENT DOCUMENTS

| | | | | |
|---|---|---|---|---|
| 5,588,838 | A | * | 12/1996 | Hansson et al. ............. 433/173 |
| 5,697,779 | A | * | 12/1997 | Sachdeva et al. .............. 433/2 |
| 6,312,259 | B1 | * | 11/2001 | Kvarnstrom et al. ........ 433/173 |
| 2001/0005575 | A1 | * | 6/2001 | Kanomi et al. ............... 433/18 |
| 2002/0182560 | A1 | * | 12/2002 | Park et al. ..................... 433/18 |

* cited by examiner

*Primary Examiner*—Cary E. O'Connor
(74) *Attorney, Agent, or Firm*—Troxell Law Office, PLLC

(57) ABSTRACT

A screw device for orthodontic treatment comprises a screw-body part, a platform part integrally formed with the screw-body part, and a head part. The head part is detachable from and exposed outside the screw-body part and is operatable to hook a spring (or rubber band) for orthodontic treatment. Since the head part is detachable, various types of head parts can be chosen to attach on the same platform part and screw-body part for performing different orthodontic treatments. Cost to manufacture the screw device is lower, and flexibility and convenience to use the screw device are higher. The screw device further comprises a detachable auxiliary unit which can be firmly clamped between the head part and platform part. The auxiliary unit has a hollow ring portion having a center hole, a first accessory member and a second accessory member. The size of the center hole is smaller than a flat cap of head part, such that it can be clamped between the head part and platform part.

9 Claims, 17 Drawing Sheets

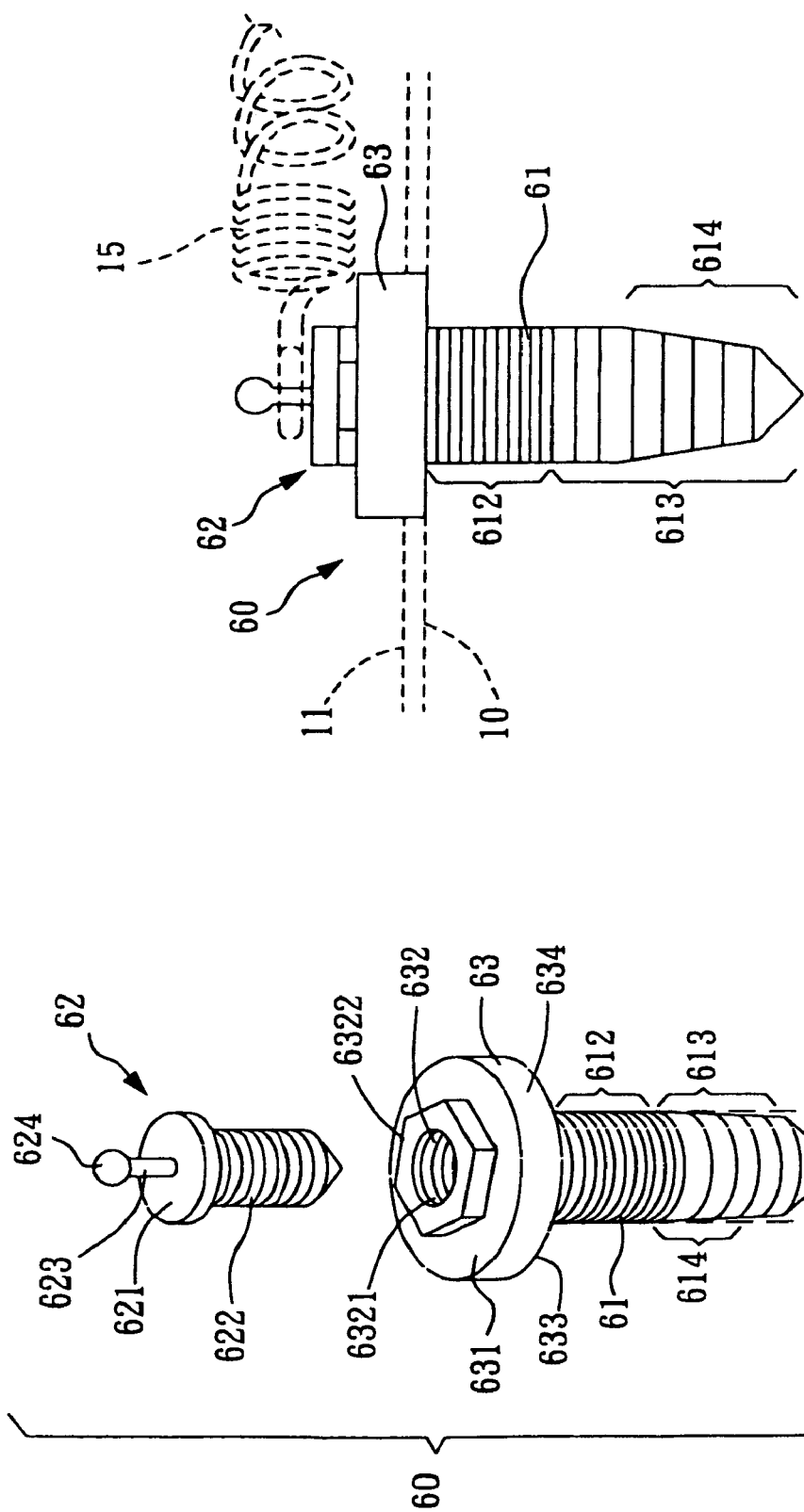

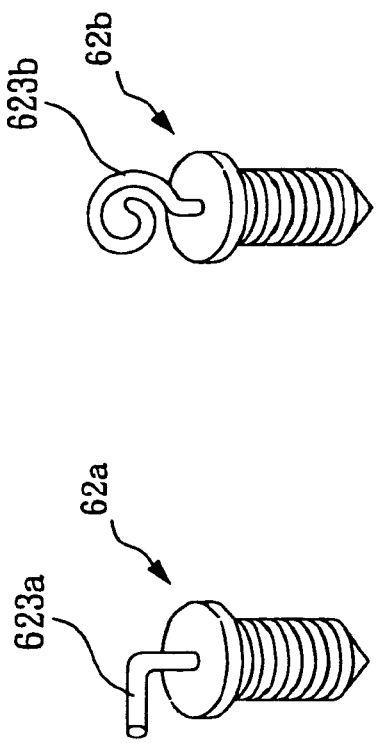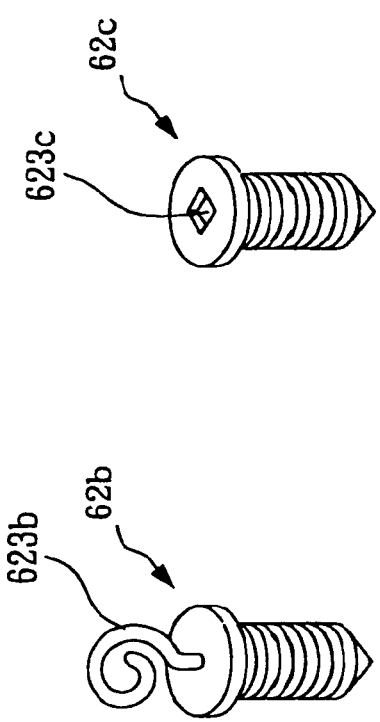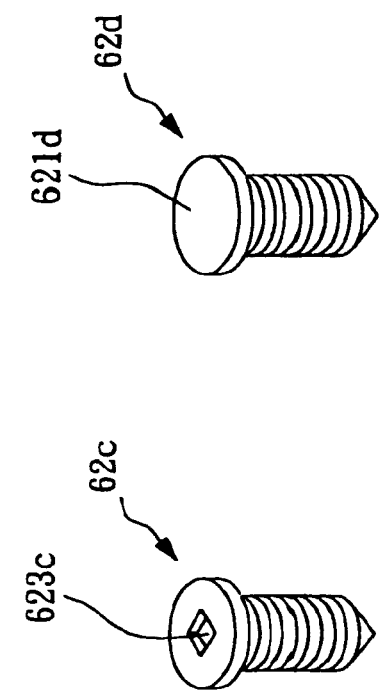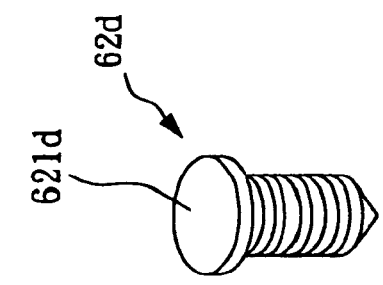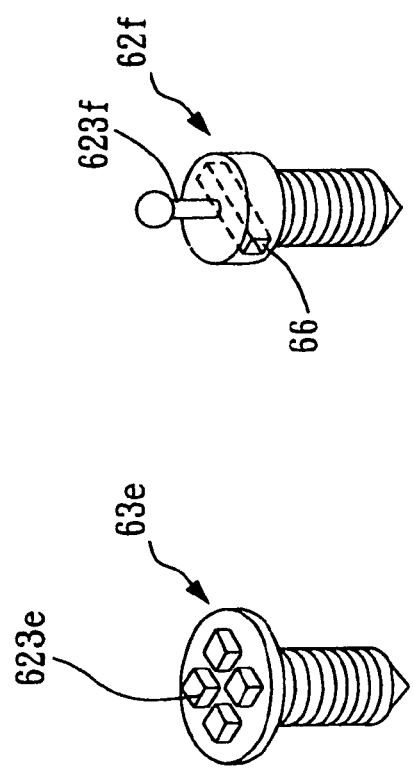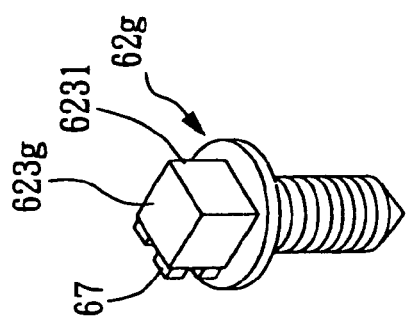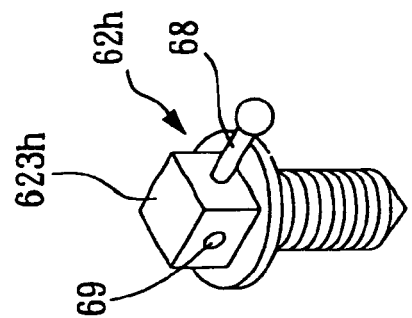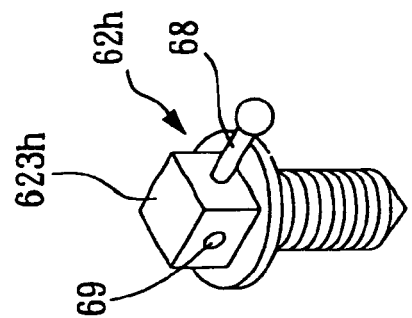

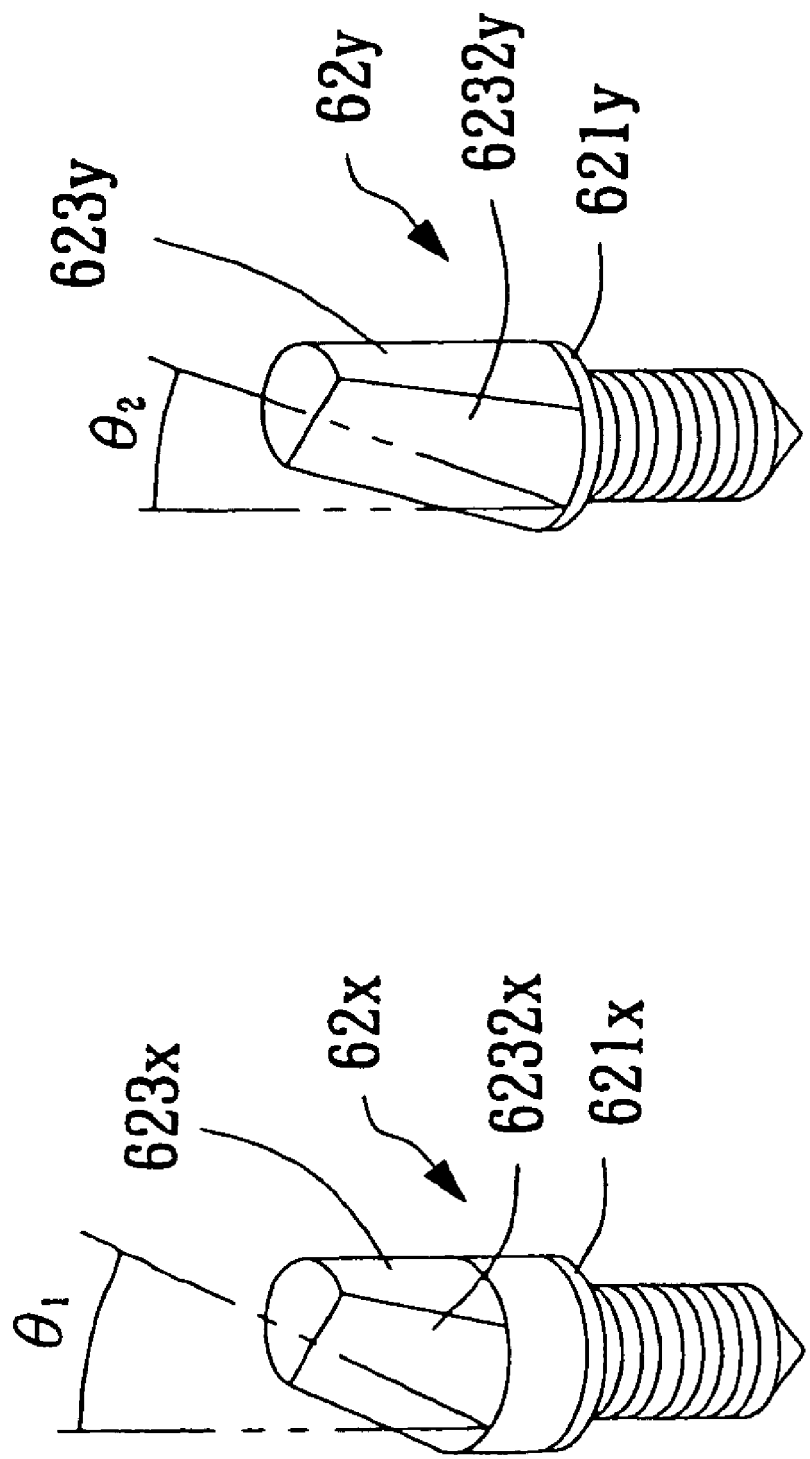

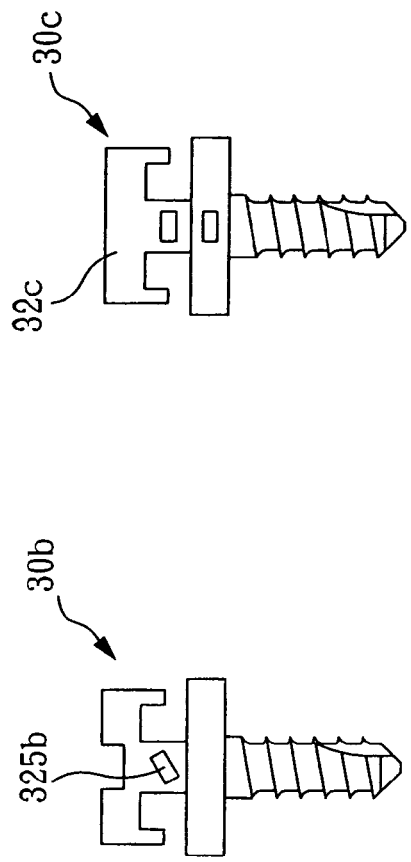
FIG. 16A
FIG. 16B
FIG. 16C
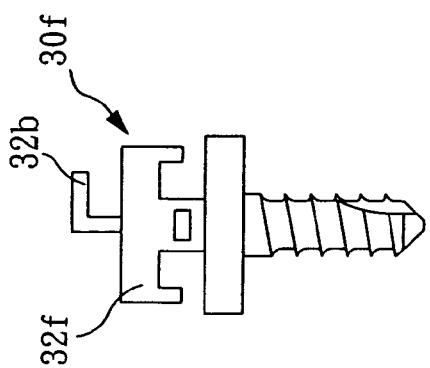
FIG. 16D
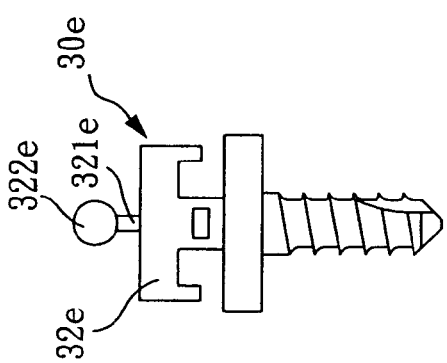
FIG. 16E
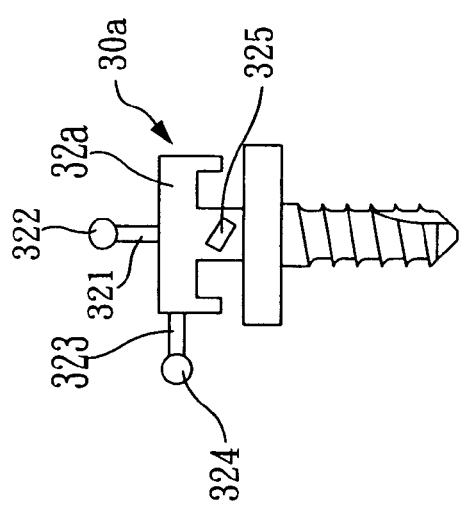
FIG. 16F
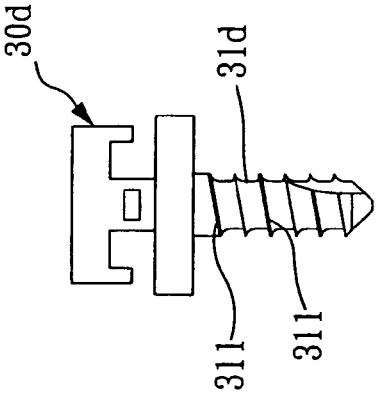

SCREW DEVICE FOR ORTHODONTIC TREATMENT

This application is a continue-in-part (CIP) application of pending U.S. patent application Ser. No. 10/885,580 filing date Jul. 8, 2004, which is yet a continue-in-part (CIP) application of pending U.S. patent application Ser. No. 10/732,292 filing date Dec. 11, 2003, which is yet a continue-in-part (CIP) application of U.S. patent application Ser. No. 10/359,577 filing date Feb. 7, 2003 which is now granted as U.S. Pat. No. 6,722,879, which is yet a continue-in-part (CIP) application of U.S. patent application Ser. No. 10/211,037 filing date Aug. 5, 2002 which is now granted as U.S. Pat. No. 6,726,475.

FIELD OF THE INVENTION

The invention relates to a screw device for orthodontic treatment, especially to a screw device that may be arranged in the maxilla (or mandible) and is capable of positioning the spring used for orthodontic treatment and accommodating the orthodontic archwire.

BACKGROUND OF THE INVENTION

As shown in FIG. 1, in a conventional orthodontic treatment process, after part of the maxilla (or mandible) 10 is cut off or a tooth 12 is pulled out (usually not the incisor), the tooth 12 or the maxilla (or mandible) 10 is pulled and dragged by an orthodontic archwire 13 after the operation for helping the maxilla (or mandible) 10 to heal over or correcting the position of the tooth 12. In order to maintain the position of the orthodontic archwire 13 relative to the tooth 12, it is usually to apply several orthodontic brackets 14 adhered onto the tooth 12, and each orthodontic bracket 14 is arranged with slot 141 for providing an accommodation for the orthodontic archwire 13. The width and the depth of the slot 141 must be slightly larger than the diameter of the orthodontic archwire 13 such that, not only may the orthodontic archwire 13 be appropriately glided along the extensive direction of the slot 141, but also may the orthodontic archwire 13 be kept from being dropped out of the slot 141.

As known in the prior arts, in order to provide a pulling-and-dragging force to the orthodontic archwire 13, a screw 20 is screwed on a maxilla (or mandible) 10 at the adjacency of a molar 121, then a spring 15 or rubber band is further connected between the screw 20 and the end of the orthodontic archwire 13 for providing an appropriate pulling-and-dragging force. Since the end of this kind of spring 15 used specially for orthodontic treatment in current market is all arranged with a hook ring 151 so, for the connection between the spring 15 and the end of the orthodontic archwire 13, the end of the orthodontic archwire 13 just may be bent into a hook structure 131, then it can be easy to fit the hook ring 151 of the spring 15 into the hook structure 131 of the end of the orthodontic archwire 13, such that both connection is completed. Relatively, the connection between the spring 15 and the screw 20 is more difficult relatively.

U.S. Pat. No. 4,988,292 discloses an abutment for orthodontic anchorage to a dental implant fixture. It comprises an endosseous implant fixture which is fixed in the lower jaw at the site of a missing molar for supporting an abutment for orthodontic anchorage. The abutment and the fixture are connected by a bolt in a detachable manner. However, the abutment of U.S. Pat. No. 4,988,292 does not provide the function of spring hooking. Even if someone tries to hook the spring on the abutment, the spring will be prone to impinge the gingival as previously illustrated. In addition, the fixture is prone to loose since it has identical outer threads and identical outer diameter throughout the entire fixture.

U.S. Pat. No. 5,836,768 discloses a fastening device for fixing orthodontic apparatuses on a dental implant. It comprises an implant which is fixed in the jaw bone, an anchoring screw screwed within an axially arranged threaded bore in the implant, and an occlusal screw located inside the threaded bore and engaged with the anchoring screw. None part of the occlusal screw nor anchoring screw is exposed outside the implant, such that they cannot be used for spring hooking. Even if the spring can be tied (not hook) on a bracket of U.S. Pat. No. 5,836,768, the spring will be prone to impinge the gingival. In addition, the implant is prone to loose since it has identical outer threads and identical outer diameter.

U.S. Pat. No. 5,921,774 discloses a supporting body for use in orthodontic appliance. It comprises a supporting body to be fixed in the jaw bone, an abutment formed with an arm at a side surface thereof, and a male screw for screwing and fixing the abutment onto the top of the supporting body. Since the screw is an independent element and is screwed from a top side of the abutment, therefore the arm can only be form at the side surface of the abutment, and thus the application and flexibility thereof are limited. In addition, the device disclosed by U.S. Pat. No. 5,921,774 comprises at least three elements (e.g., supporting body, abutment and male screw). Not only the cost to manufacture is higher, but also is more complex to use. Moreover, the supporting body is prone to loose since it has identical outer threads (or no threads at all) and identical outer diameter throughout the entire supporting body.

Other prior art, such like U.S. Pat. No. 6,241,516, U.S. Pat. No. 5,071,345, and US Pub. No. 2002/0127510. None of them has been disclosed a screw device which comprises a screw-body part, a platform part and a head part which is detachable from and exposed outside the platform part (or screw-body part) and is operatable to hook the spring for orthodontic treatment.

As known from above description, the prior arts that are used for orthodontic treatment currently still have many shortcomings to be further improved urgently.

Publication No. US 2003/00224315 A1 and Publication No. US 2003/0023182 A1 are two patent applications filed by the same inventor of the present invention, which disclosed some embodiments of improved screw devices for facilitating orthodontic treatments.

SUMMARY OF THE INVENTION

The main objective of the invention is to provide an improvement for a screw device for orthodontic treatment. The screw device in accordance with the present invention comprises a screw-body part, a platform part and a head part. The head part is detachable from and exposed outside the platform part and is operatable to hook the spring for orthodontic treatment.

Preferably, the threads of the screw-body part are divided into at least a first thread portion located near to the platform part and a second thread portion located away from the platform part. The threads of the first thread portion are designed to have relatively narrower width and smaller pitch, while the threads of the second thread portion have wider width and larger pitch.

Preferably, the screw device further comprises a detachable auxiliary unit which can be firmly clamped between the head part and platform part. The auxiliary unit has a hollow ring portion having a center hole, a first accessory member and a second accessory member. The size of the center hole is smaller than a flat cap of head part, such that it can be clamped between the head part and platform part.

Preferably, some of the external threads of the screw-body part are painted with different colors. These color-painted threads are spaced apart from each other with predetermined distance (for example, 0.5 mm or other scale) such that they can act like scales to indicate how deep this screw device is fastened.

For further understanding the objects, the characteristics, and the functions of the structures of the present invention, a detailed description matched with corresponding drawings are presented as follows.

BRIEF DESCRIPTION OF THE DRAWINGS

FIG. 2 is a perspective view of the first preferred embodiment of the screw device for orthodontic treatment according to the present invention.

FIG. 3 is a front view of the first preferred embodiment shown in FIG. 2, wherein the head part 62 is attached onto the platform part 63 of the screw device 60.

FIGS. 4A~4J are some preferred embodiments of the head parts 62a~62h, 62x and 62y which can be fixed to the platform part 63 and screw-body part 61 as shown in FIG. 2 of the present invention.

FIGS. 16A~16F illustrate various designs of the screw devices 30a~30f in accordance with the present invention.

FIG. 20 shows the embodiment that the first and second accessory members 553a, 554a are detachable from the ring portion 551a of auxiliary unit 55a.

DETAILED DESCRIPTION OF THE INVENTION

Figure 1:
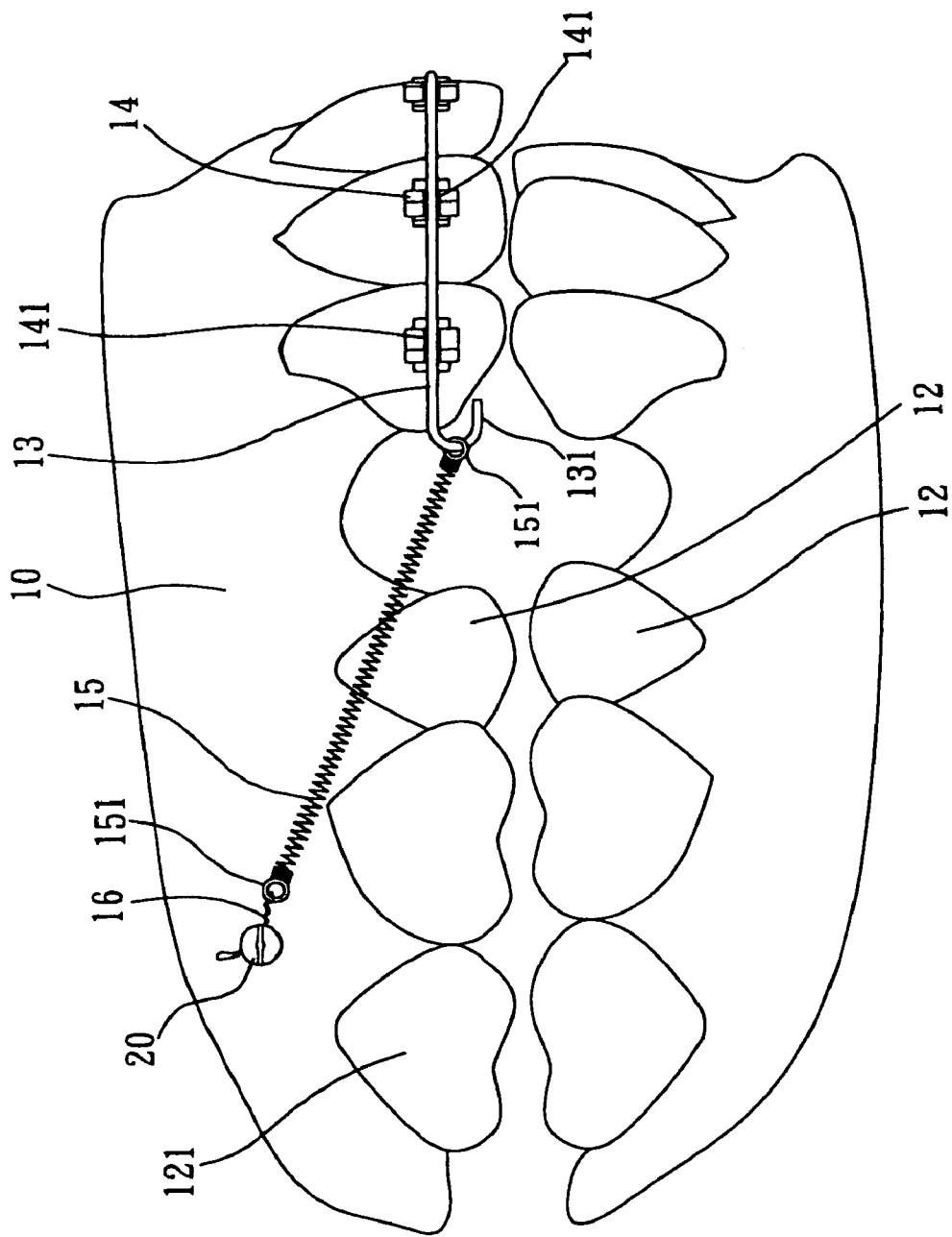
FIG. 1 is an embodiment illustration for a screw device, according to the prior arts, arranged in the mouth for orthodontic treatment.

The elements described thereinafter, such as: maxilla (or mandible) 10, gingiva 11, tooth 12, orthodontic archwire 13, orthodontic bracket 14, and spring 15 (or rubber band) for orthodontic treatment etc., and their relative position arranged in the mouth are all similar to the prior arts shown in FIG. 1 and they are not the technical characteristics of the invention, so they will be given same element names and referential numbers and their detailed composition, arrangement position, and function are not described herein repetitiously. One thing is worth mentioning: although the embodiment of the prior arts shown in FIG. 1 only depicts an embodiment that a correction device is arranged on the outside of the upper jaw, however, it may also be arranged on the outside or inside surface of maxilla (or mandible).

Please refer to FIG. 2 and FIG. 3. FIG. 2 is the first preferred embodiment for the screw device according to the invention for orthodontic treatment. FIG. 3 is a schematic drawing showing the screw device of FIG. 2 being fixed on the maxilla (or mandible) for orthodontic treatment.

As shown in FIG. 2 and FIG. 3, the first preferred embodiment of the screw device 60 in accordance with the present invention comprises: a screw-body part 61, a platform part 63 and a head part 62. The screw-body part 60 has a diameter with external threads extending a length. The platform part 63 is axially aligned and integrally formed with the screw-body part 61 to be a single element. The head part 62 is separately manufactured and is an independent element.

In this preferred embodiment, the external threads of the screw-body part 61 are slightly loosened at a portion 613 away from the platform part 63 and are relatively concentrated at another portion 612 near to the platform part 63. In addition, the screw-body part 61 is tapered at a section 614 away from the platform part 63. In one embodiment, the tapered section 614 of the screw-body part 61 has a tapering angle of around 2~10 degrees. By such arrangement, the user (for example, a dentist) will be easy to operate at the beginning when he/she starts screwing the screw device 60 into an object (for example, the maxilla or mandible of a patient). It is because the bottom tip (i.e., section 614) of the screw-body part 61 is narrower and the threads on that portion 613 are relatively loosened, such that the user does not need much effort/strength to screw it. When the user is about to screw the entire screw-body part 61 into the object, the gradually enlarged diameter and concentrated threads (at portion 612) of the screw-body part 61 will provide more tightened and secured fixing result. Of course, the user will need relatively more effort/strength to screw it when the top portion 612 of the screw-body part 61 entering the object. The other advantage for designing the screw-body part 61 with loosened threads and tapered end is that, since the maxilla/mandible of human includes a relatively fragile inner structure and a relatively hard and firm outer structure. The loosened threads and tapered end of the screw-body part 61 can prevent the fragile inner structure of the maxilla/mandible being damaged, while a firm fixing result can still be obtained when the screw-body part 61 is almost entirely screwed into the maxilla/mandible. In addition, the outer surface of the screw-body part 61 (e.g. surfaces of threads) can be roughened to increase friction between the screw-body part 61 and the object (e.g. the maxilla or mandible), such that the screw device 60 of the present invention can be fixed on the object even firmer. Methods for roughening the surfaces of threads include chemical etching and other conventional techniques. Conventional HA particles can also be applied on the surfaces of threads to improve the biointegration effect.

The platform part 63 further comprises a flat top plane 631, a first mating structure 632, a flat bottom plane 633 and an outer periphery 634. In this embodiment, the platform part 63 has a width larger than the width of the screw-body part 61 and the width of the head part 62. The outer periphery 634 is a smooth surface without threads thereon. The shape of the outer periphery 634 can be either round shaped as shown in FIG. 2 or polygon shaped (i.e., being a polygon from the top view thereof). The flat top plane 631 is perpendicular to the screw-body part 61. The first mating structure 632 is formed on the flat top plane 631 and comprises a screw hole 6321 and a nut contour 6322. The screw hole 6321 is for fixing the head part 62. The nut contour 6322 allows the user to use a tool to screw the screw-body part 61 into the object. The flat bottom plane 633 is adjacent to the top end of the screw-body part 61 and is perpendicular to the screw-body part 61, such that when the screw-body part 61 is entirely screwed into the object, the bottom plane 633 will contact a surface of the object (maxilla/mandible 10), as which shown in FIG. 3. As a result, not only the screw device can be fixed firmly, but also the gingiva 11 can recover rapidly and beautifully. Of course, it is also possible for a user (dentist) not to screw the entire screw-body part 61 into the object (maxilla/mandible 10). In this circumstance, there will be a gap between the bottom plane 633 and the object (maxilla/mandible 10). However, since the bottom plane 633 is a flat surface and the outer periphery 634 is a smooth surface, they can still help the gingiva 11 to recover well.

The head part 62 is detachable from the platform part 63 and further comprises a flat cap 621, a second mating structure 622 and an accessory member 623. The second mating structure 622 is formed on a bottom side of the flat cap 62. The second mating structure 622 is capable of engaging with the first mating structure 632 so as to fix the head part 62 onto the platform part 63. In this preferred embodiment, the second mating structure 622 is a screw. The accessory member 623 is formed on a top side of the flat cap 621 for assisting orthodontic treatment. The accessory member 623 is exposed outside of the platform part 63 when the second mating structure 622 engages with the first mating structure 632, such that operations of orthodontic treatment are possible to be performed on the accessory member 623. In the preferred embodiment, the accessory member 623 is formed as a rod-like neck with a uniform width. The neck (accessory member 623) is axially aligned with the screw-body part 61 and extends outwardly from the top side of the flat cap 621 at a first end thereof. The neck (accessory member 623) is configured to removably hook one end of the spring 15. A ball head 624 is located at the top end of the accessory member 623. The ball head 624 has a diameter larger than which of the neck so as to prevent the spring 15 from dropping. The reason why the rod-like neck is axially aligned with the screw-body part 61 and extends outwardly from the top side of the flat cap 621 is that, the thickness of the platform part 63 can act as a protector to prevent the spring 15 from damaging the tissues of the gingiva 11.

FIGS. 4A~4J are some preferred embodiments of the head parts 62a~62h, 62x and 62y which can be fixed to the platform part 63 and screw-body part 61 of the present invention. Because the head part 62 of the present invention is detachable and changeable, it is possible to design various types of head parts 62a~62h, 62x and 62y to mate with the same type of platform part 63 and screw-body part 61 so as to achieve different purposes of orthodontic treatments. Flexibility and convenience for using the screw device 60 are increased. In the mean time, only one type of platform part 63 and screw-body part 61 is needed to be manufactured, thus cost to make screw devices with different functions is decreased. As shown in FIG. 4A, the accessory member 623a of the head part 62a is formed as an L-shaped structure. In FIG. 4B, the accessory member 623b of the head part 62b is formed as a hook shaped structure. In FIG. 4C, the accessory member 623c of the head part 62c is a concave formed on the top surface of the head part 62c. The concave (623c) can be used to fill with adhesive to attach an additional component (not shown) for orthodontic treatment as required, for example, an orthodontic bracket or etc. In FIG. 4D, there is no accessory member being formed on the head part 62d, such that the top surface of the flat cap 621d is a plane. User (dentist) can attach an additional component on the top surface of the flat cap 621d if required. In FIG. 4E, the accessory member 623e of the head part 62e is an orthodontic bracket for accommodating an orthodontic arch-wire (not shown). In FIG. 4F, the accessory member 623f of the head part 62f is a rod-like neck as which shown in FIG. 2. However, the flat cap 621f of this embodiment is thicker and is formed with a rectangular through hole 66 for allowing an orthodontic archwire to pass therethrough. In FIG. 4G, the accessory member 623g of the head part 62g is a cubic having a plurality of flat side surfaces 6231. An additional component, such like an orthodontic bracket 67, can be adhered to one of the flat side surfaces 6231 to assist orthodontic treatment. In FIG. 4H, the accessory member 623h of the head part 62h is a cubic having a rod-like neck 68 formed on a side surface thereof for hooking a spring. The cubic is further formed with a round through hole 69 for allowing an orthodontic archwire to pass therethrough. In FIG. 4I, the accessory member 623x of the head part 62x has an inclined plane 6232x located on the flat cap 621x. There is an inclined angle $\theta_1$ between the axis of the second mating structure (e.g. the screw) and the inclined plane 6232x. Users (for example, orthodontic doctors) can attach additional component on the inclined plane 6232x for assisting orthodontic treatment. In a preferred embodiment, the inclined angle $\theta_1$ can be 30°, 45°, 60° or other angles. FIG. 4J shows yet another embodiment of the head part 62y in which the inclined plane 6232y of the accessory member 623y has an even smaller inclined angle $\theta_2$. The inclined angle $\theta_2$ is typically smaller than 30° in this embodiment. In addition, the flat cap 621y has a thickness smaller than which of the FIG. 4I.

Figure 5:
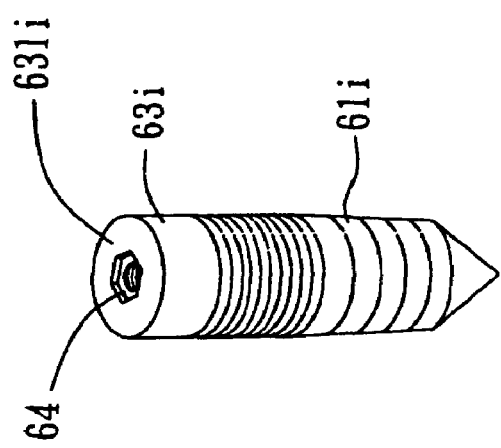
FIG. 5 is the second preferred embodiment of the screw-body part 61i and platform part 63i of the screw device according to the present invention.

FIG. 5 is the second preferred embodiment of the screw-body part 61i and platform part 63i in accordance with the present invention. In this embodiment, the platform part 63i has a diameter equal to which of the screw-body part 61i. In addition, the flat top plane 631i of the platform part 63i is formed with a nut-shaped bore 64 for allowing a tool, such like a driver, to mate therewith.

Figure 6:
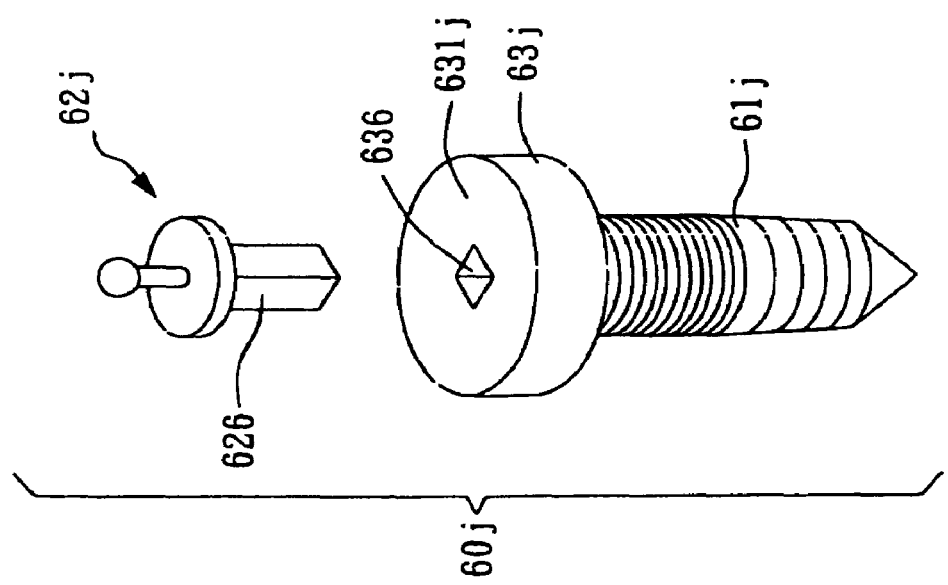
FIG. 6 is the third preferred embodiment of the screw device 60j according to the present invention.

FIG. 6 is the third preferred embodiment of the screw device 60j according to the present invention. In this embodiment, the first mating structure is a polygon shaped bore 636 formed on the flat top plane 631j of the platform part 63j. The polygon shaped bore 636 is aligned with the screw-body part 61*j*. In addition, the second mating structure of the head part 62*j* is a polygon shaped pillar 626 which can be plugged into and fixed firmly with the polygon shaped bore 636 by adhesive.

Figure 7:
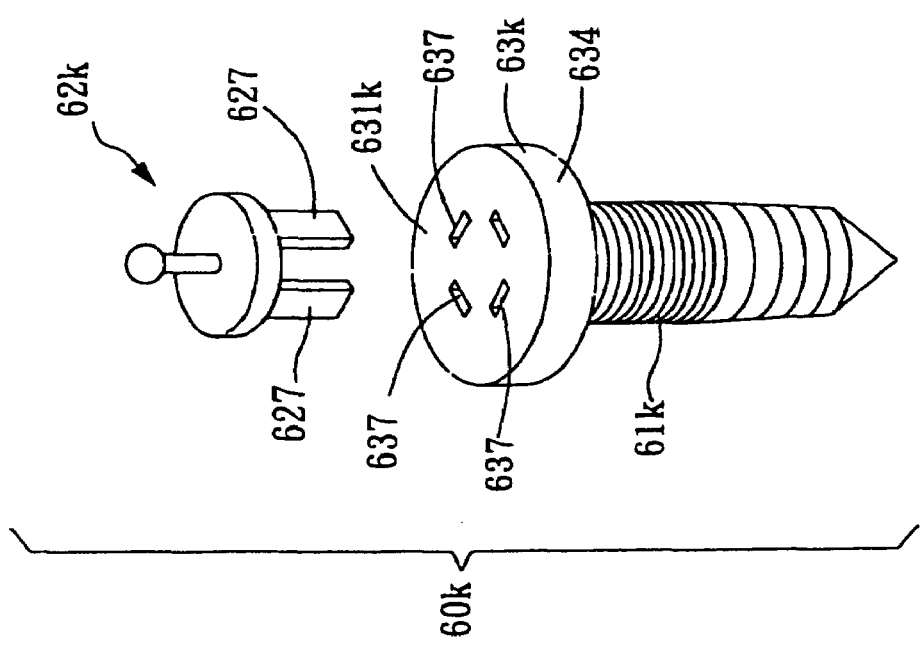
FIG. 7 is the fourth preferred embodiment of the screw device 60k according to the present invention.

FIG. 7 is the fourth preferred embodiment of the screw device 60*k* according to the present invention. In this embodiment, the first mating structure includes a plurality of sockets 637 formed on the flat top plane 631*k* of the platform part 63*k*. The second mating structure of the head part 62*k* is a plurality of plugs 627 which are so shaped and positioned that they can be plugged into and fixed firmly with the sockets 637 by adhesive.

Figure 8:
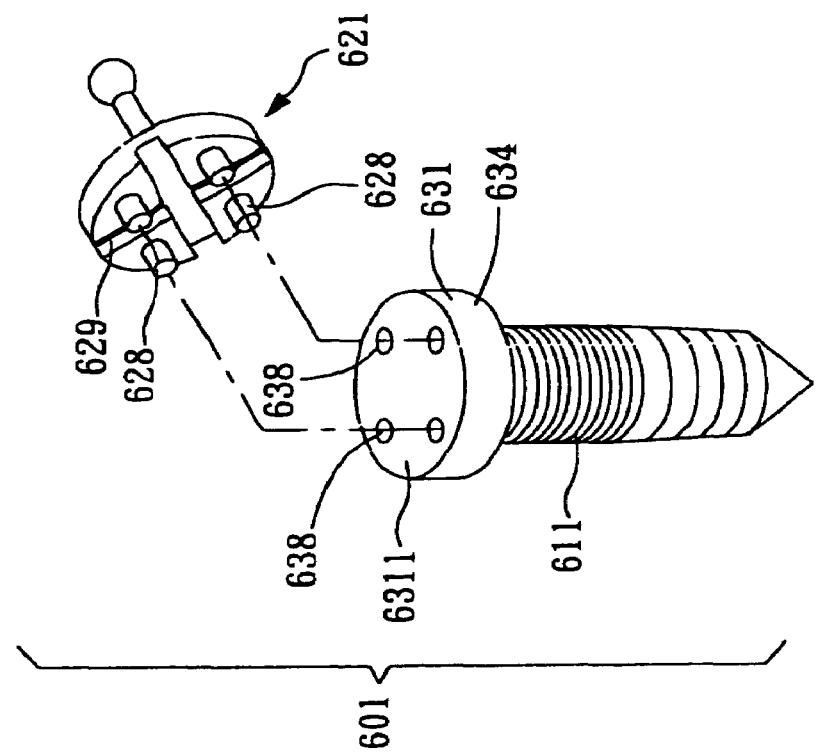
FIG. 8 is the fifth preferred embodiment of the screw device 60l according to the present invention.

FIG. 8 is the fifth preferred embodiment of the screw device 601 according to the present invention. In this embodiment, the first mating structure includes a plurality of pin holes 638 formed on the flat top plane 631*l* of the platform part 631. The second mating structure of the head part 621 is a plurality of pins 628 which are so shaped and positioned that they can be plugged into and fixed firmly with the sockets 638 by adhesive. In addition, the head part 621 is formed with a crisscross-shaped rectangular groove 629 on a surface thereof facing the flat top plane 631*l* of the platform part 631. Such that, when the head part 621 is fixed to the platform part 631, the crisscross-shaped rectangular groove 629 substantially becomes two rectangular through holes (intersecting with each other) for allowing the orthodontic archwire to pass therethrough.

Figure 9:
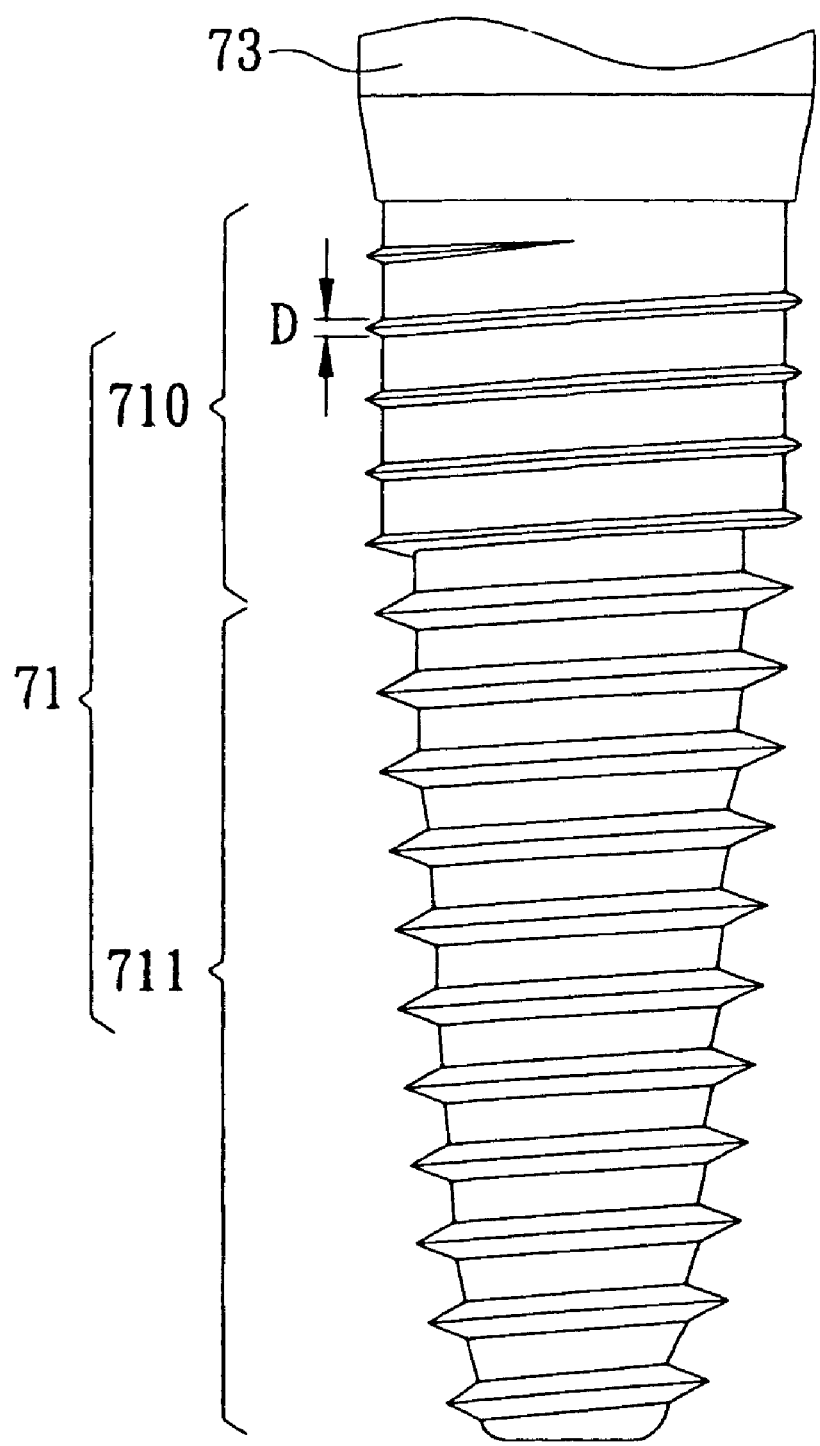
FIG. 9 is the sixth preferred embodiment of the screw-body part 71 of the screw device for orthodontic treatment of the present invention.

FIG. 9 is the sixth preferred embodiment of the screw-body part 71 of the screw device of the present invention. In this preferred embodiment, the threads of the screw-body part 71 can be divided into two or more groups, namely the first thread portion 710 which is located near to the platform part 73, and the second thread portion 711 located away from the platform part. The threads of the first thread portion 710 are designed to have relatively narrower width "D" and smaller pitch, while the threads of the second thread portion 711 have wider width and larger pitch. Typically, the width "D" of the threads of the first thread portion 710 can be between D=0.5~0.75 mm, while the width of the threads of the second thread portion 711 are larger than 0.75 mm. By applying such kind of configuration to the threads of the screw-body part 71, there will be more numbers of threads of the first thread portion 710 being engaged with the relatively firm outer structure of the maxilla/mandible of human being, so as to fix the screw-body part 71 into the maxilla/mandible tightly.

Figure 10:
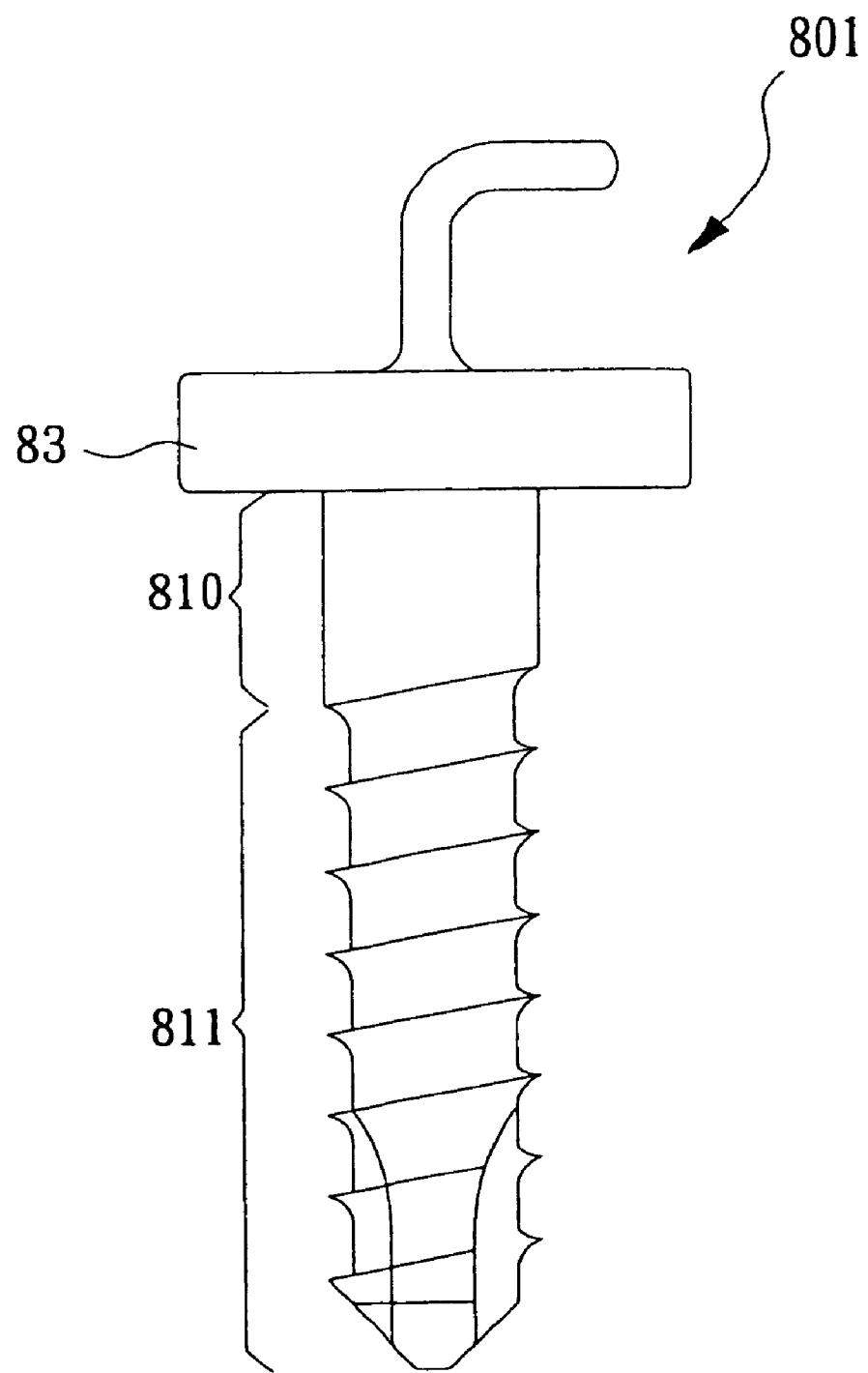
FIG. 10 is the seventh preferred embodiment of the screw device 801 of the present invention.

FIG. 10 is the seventh preferred embodiment of the screw device 801 of the present invention. In this preferred embodiment, the screw-body part includes a section 810 without any threads thereon at a location near to the platform part 83. Therefore, there exists a no-thread section 810 between the threads 811 and the platform part 83. The no-thread section 810 provides a smooth contact with the soft tissues located on the top surfaces of the maxilla/mandible after the screw device 801 is screwed into the maxilla/mandible. For some specific applications or some specific patients where/whose outer structures of the maxilla/mandible are fragile, the no-thread section 810 of the screw-body part can prevent the fragile structures of the maxilla/mandible being damaged by the threads.

Figure 11A:
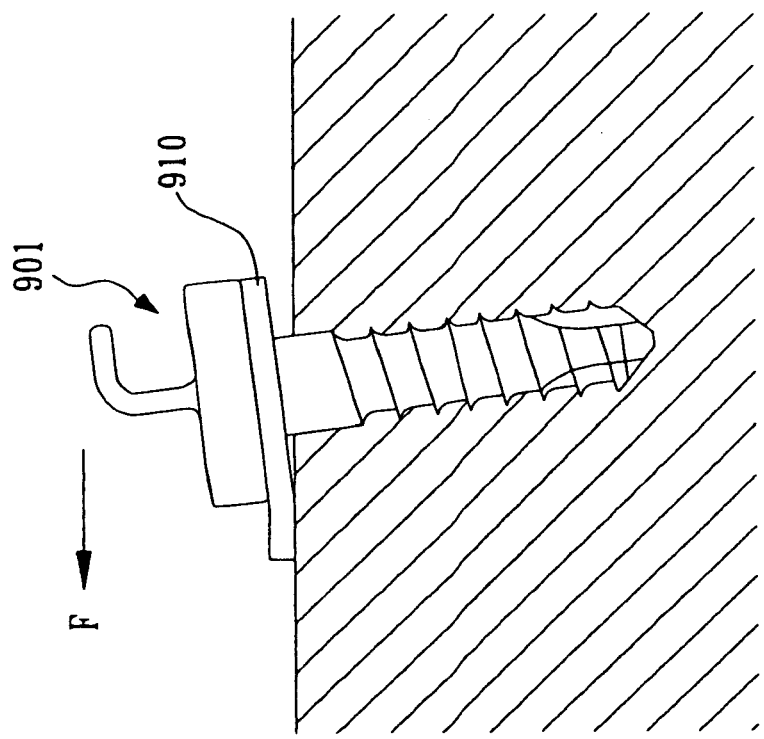
FIG. 11A and FIG. 11B are the eighth preferred embodiment of the screw device 901 of the present invention.
Figure 11B:
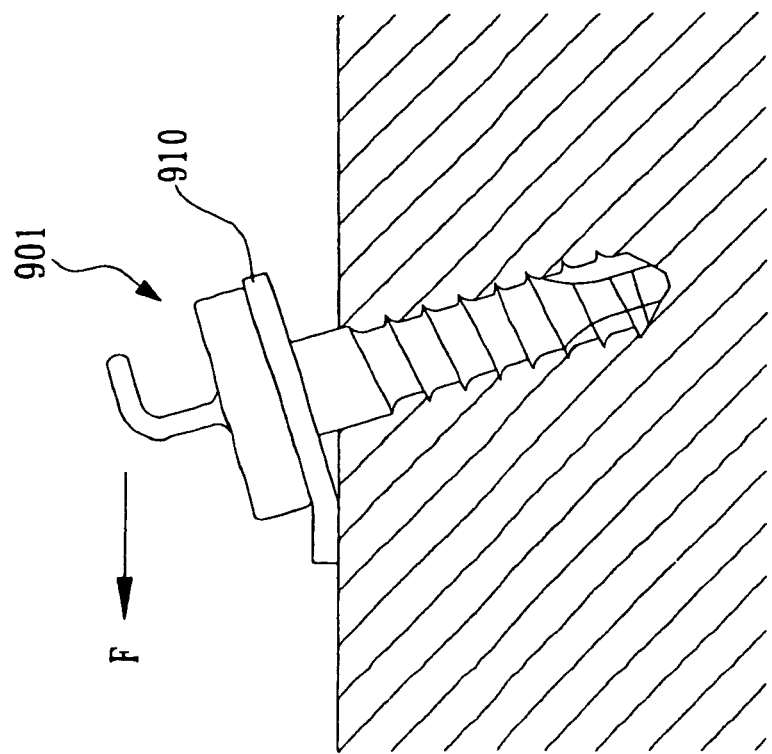

FIG. 11A and FIG. 11B are the eighth preferred embodiment of the screw device 901 of the present invention. In this preferred embodiment, an additional washer 910 is provided beneath the bottom surface of the platform part. The washer 910 is typically useful when the screw device 901 is crewed into the maxilla/mandible in an inclined angle. When the screw device 901 is screwed into the maxilla/mandible, the washer 910 is compressed, such that an internal force generated by the washer 910 will make the threads of the screw-body part of the screw device 901 to engage with the maxilla/mandible more firmly. The screw device 901 will not tend to loose even it is subject to a pulling force "F" resulted from an orthodontic spring (not shown in this figure).

Figure 12:
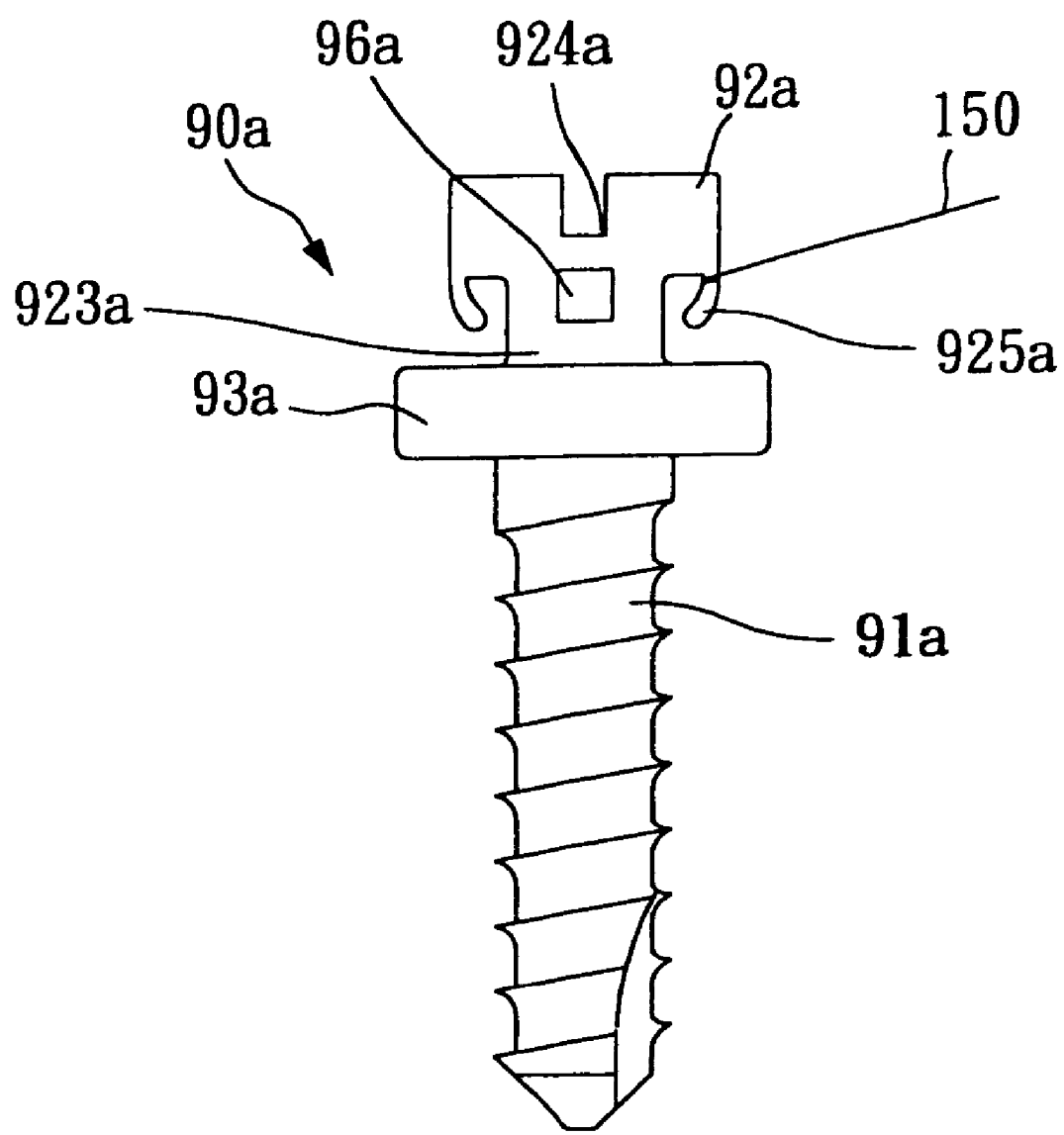
FIG. 12 is the ninth preferred embodiment of the screw device 90a of the present invention.

FIG. 12 is the ninth preferred embodiment of the screw device 90*a* of the present invention. The screw device 90*a* also comprises: a screw-body part 91*a*, a platform part 93*a* and a head part 92*a*. The screw-body part 91*a*, platform part 93*a* and head part 92*a* are integrally formed as a single element in this embodiment. A rectangular through hole 96*a* is formed at the neck portion 923*a* of the screw device 90*a* for allowing an orthodontic archwire to pass therethrough. The head part 92*a* is further formed with an orthodontic bracket 924*a* for accommodating an orthodontic archwire (not shown), a neck portion 923*a* for hooking an orthodontic spring (not shown), and a concave 925*a* extending downward from the bottom side of the orthodontic bracket 924*a*. The concave 925*a* allows the user to tie one end of stainless wires 150 or rubber bands onto the concave 925*a*, while to tie the other end of the stainless wires 150 or rubber bands onto the orthodontic archwire located on the orthodontic bracket 924*a*, so as to position the orthodontic archwire on the orthodontic bracket 924*a* firmly.

Figure 13:
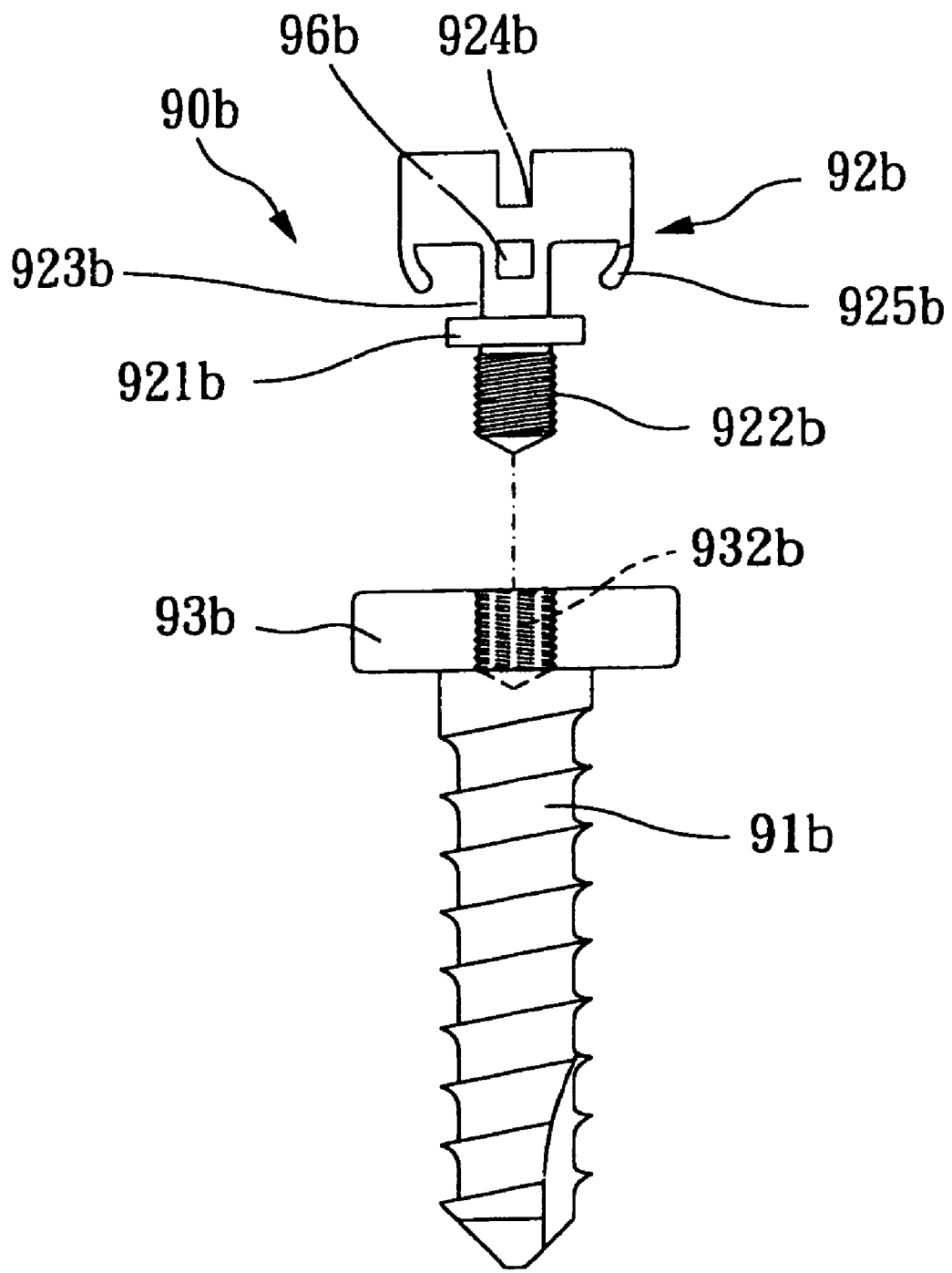
FIG. 13 is the tenth preferred embodiment of the screw device 90b of the present invention.

FIG. 13 is the tenth preferred embodiment of the screw device 90*b* of the present invention. The screw device 90*b* comprises: a screw-body part 91*b*, a platform part 93*b* and a head part 92*b*. In this preferred embodiment, the head part 92*b* is an independent component and is detachable from the platform part 93*b* of the screw device 90*b*. The head part 92*b* is further formed with a flat cap 921*b*, a second mating structure 922*b*, a neck portion 923*b*, an orthodontic bracket 924*b*, and a concave 925*b*. The platform part 93*b* is further formed with a first mating structure 932*b* for engaging with the second mating structure 922*b*. A rectangular through hole 96*b* is formed in the neck portion 923*b* of the screw device 90*b* for allowing an orthodontic archwire to pass therethrough.

Figure 14B:
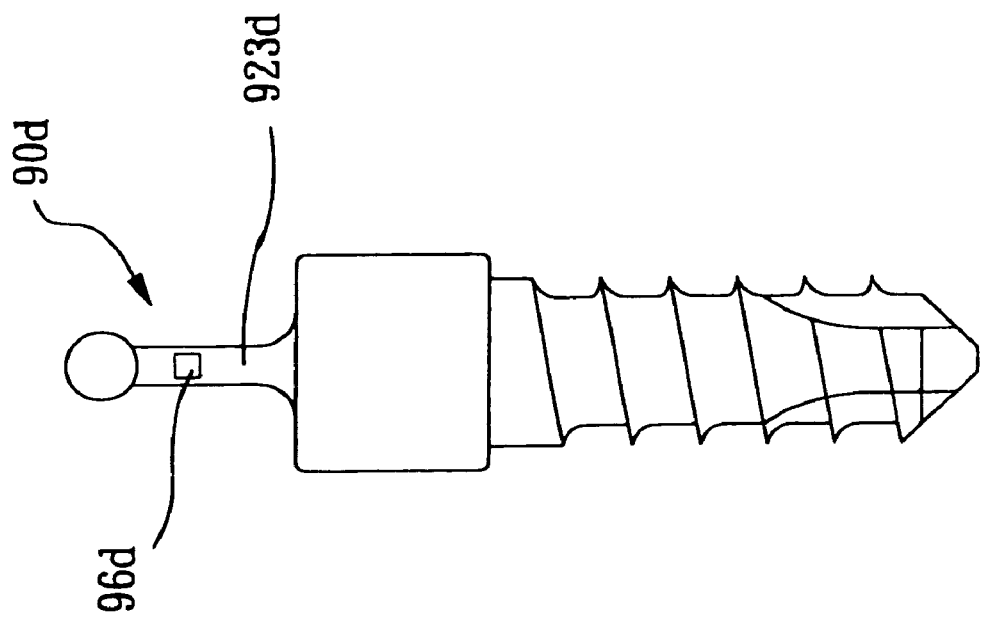
FIG. 14B is the twelfth preferred embodiment of the screw device 90d of the present invention.
Figure 14A:
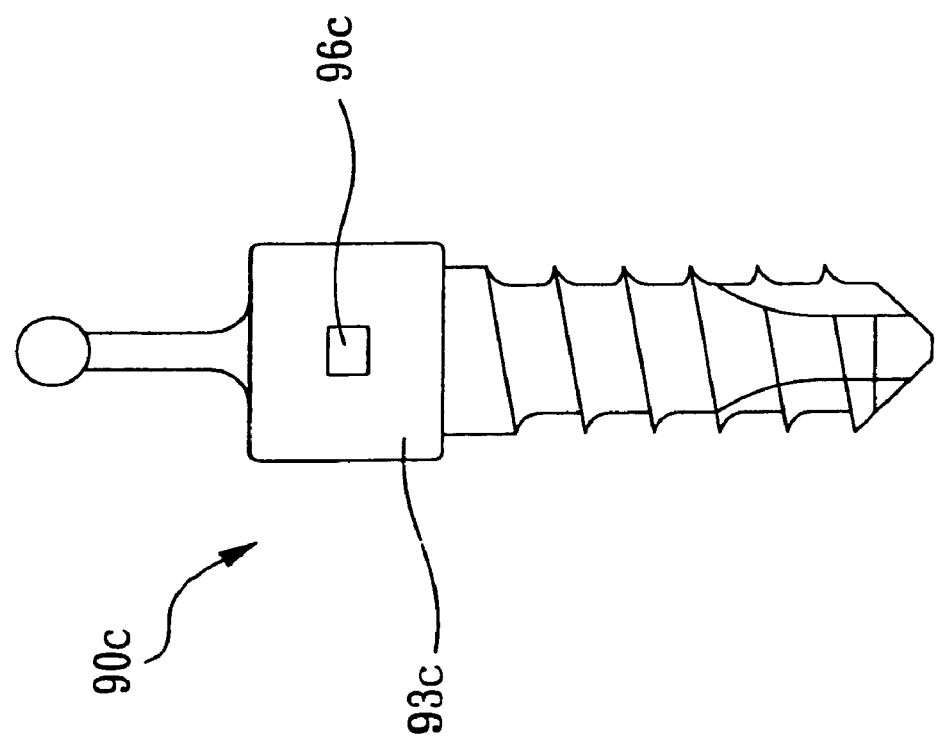
FIG. 14A is the eleventh preferred embodiment of the screw device 90c of the present invention.

FIG. 14A and FIG. 14B are the eleventh and the twelfth preferred embodiments of the screw devices 90*c*, 90*d* of the present invention. In the preferred embodiment shown in FIG. 14A, a rectangular through hole 96*c* is further formed in the platform part 93*c* of the screw device 90*c* for allowing an orthodontic archwire to pass therethrough. In FIG. 14B, a rectangular through hole 96*d* is formed in the neck portion 923*d* of the screw device 90*d* for allowing an orthodontic archwire to pass therethrough. The screw devices 90*c*, 90*d* can either be integrally formed, or have detachable head parts as previously described.

Figure 15:
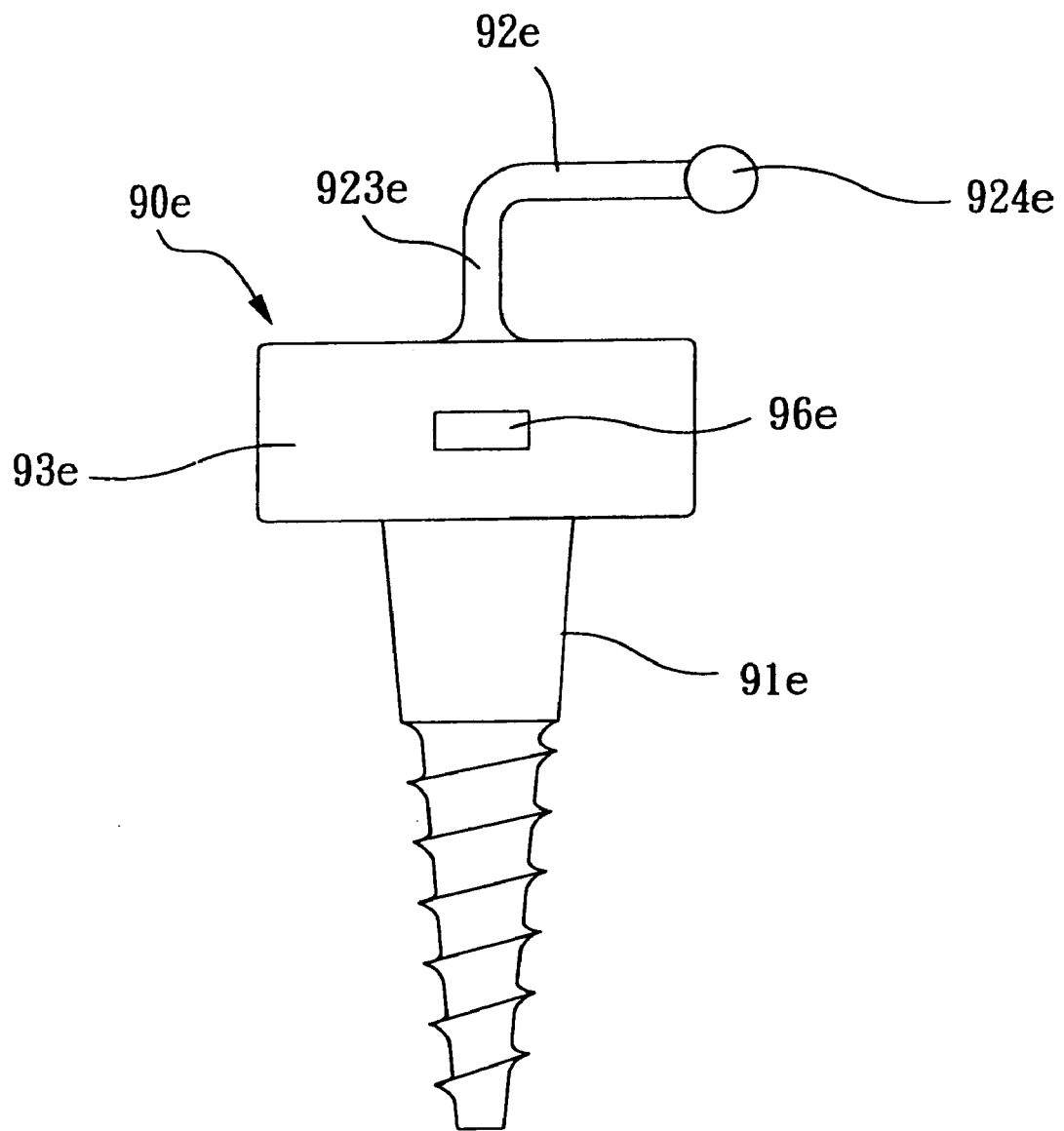
FIG. 15 is the thirteenth preferred embodiment of the screw device 90d of the present invention.

FIG. 15 is the thirteenth preferred embodiment of the screw device 90*e* of the present invention. The screw device 90*e* comprises: a screw-body part 91*e*, a platform part 93*e* and a head part 92*e*. The head part 92*e* has a neck portion 923*e* which is bended as a L-shaped structure. A ball head 924*e* having a diameter greater than the neck portion is formed on the free end of the neck portion 923*e* such that the orthodontic spring will not drop off when it is hooked on the neck portion 923*e*. The screw-body part 91*e* is tapered and includes a no-thread section near to the platform part 93*e*. A rectangular through hole 96*e* is formed in the platform part 93*e* for allowing an orthodontic archwire to pass therethrough.

FIGS. 16A~16F illustrate various designs of the screw devices 30*a*~30*f* in accordance with the present invention. Because the screw devices 30*a*~30*d* shown in FIGS.

16A~16F are almost exactly the same as the screw device 90a shown in FIG. 12, therefore, only the differences will be illustrated herein. In FIG. 16A, the head part 32a of screw device 30a does not include an orthodontic bracket but is formed with two accessory members 321, 322 extending upward and sideward respectively. Each of the accessory members 321, 323 has a ball head 322, 324 on its top end. In addition, the rectangular through hole 235 is inclined. In FIG. 16B, the screw device 30b is almost identical with the screw device 90a of FIG. 12, only that the rectangular through hole 235b of screw device 30b is inclined. In FIG. 16C, the screw device 30c is almost identical with the screw device 90a of FIG. 12, only that the top surface of the head part 32c of screw device 30c does not include an orthodontic bracket but is merely a flat top. In addition, both the platform part and neck portion are formed with a rectangular through hole respectively. In FIG. 16D, the screw device 30d is almost identical with the screw device 30c shown in FIG. 16C, only that some of the external threads 311 of the screw-body part 31d are painted with different colors. These color-painted threads 311 are spaced apart from each other with predetermined distance (for example, 0.5 mm or other scale) such that they can act like scales to indicate how deep this screw device 32d is fastened. In FIG. 16E, the head part 32e of screw device 30e does not include an orthodontic bracket but is formed with one accessory member 321e extending upward having a ball head 322e. In FIG. 16F, the head part 32f of screw device 30f does not include an orthodontic bracket but is formed with an L-shaped accessory member 326.

Figure 17B:
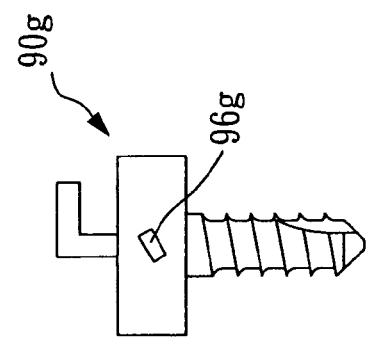
FIGS. 17A~17B illustrate various designs of the screw devices 90f, 90g in accordance with the present invention.
Figure 17A:
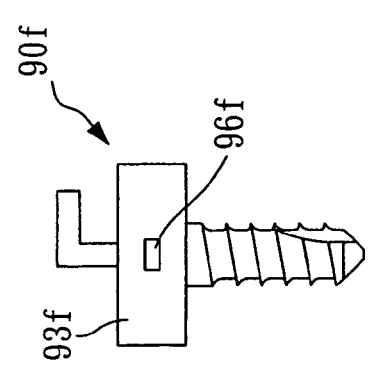

FIGS. 17A~17B illustrate various designs of the screw devices 90f, 90g in accordance with the present invention. Because the screw devices 90f, 90g shown in FIGS. 17A~17B are almost exactly the same as the screw device 90e shown in FIG. 15, therefore, only the differences will be illustrated herein. In FIG. 17A, the screw device 90f is almost identical with the screw device 90e of FIG. 15, only that the rectangular through hole 96f formed in the platform part 93f is extending vertically but not horizontally. However, as shown in FIG. 17B, the rectangular through hole 96g of screw device 90g can also be inclined.

Figure 18B:
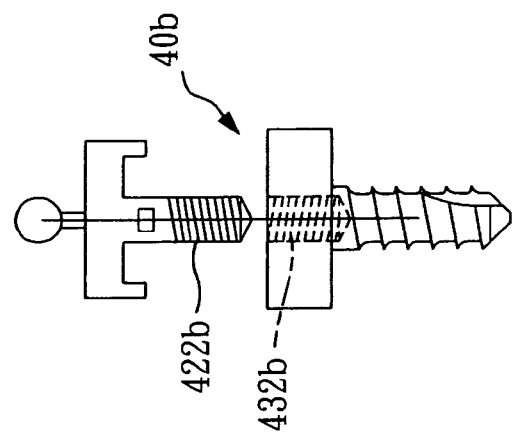
FIGS. 18A~18B illustrate various designs of the screw devices 40a, 40b in accordance with the present invention.
Figure 18A:
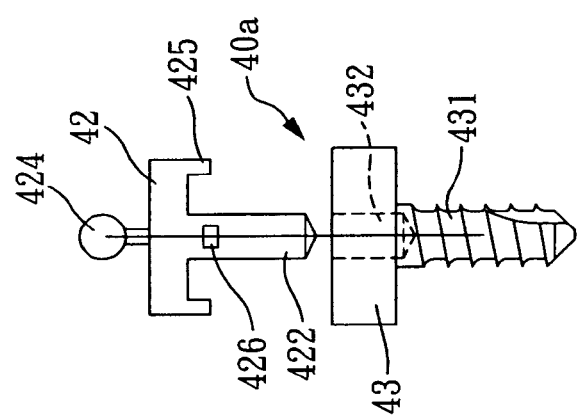

FIGS. 18A~18B illustrate various designs of the screw devices 40a, 40b in accordance with the present invention. Because the screw devices 40a, 40b shown in FIGS. 18A~18B are mostly similar to screw device 60 shown in FIG. 2, therefore, only the differences will be illustrated herein. In FIG. 18A, the head part 42 of screw devices 40a is formed with a concave 425 at the bottom side of the head part 42, which is similar to the concave 925a of FIG. 12. An accessory member 424 having a ball head is formed on the top side of the head part 42. The first and second mating structures 432, 422 are not threaded, but the second mating structure 422 of head part 42 can be plugged into and fixed firmly with the first mating structure 432 of platform part 43 by adhesive. A rectangular through hole 426 is further formed in the second mating structure 422. When the second mating structure 422 is plugged in the first mating structure 432, the rectangular through hole 426 is still exposed outside. In addition, the external threads of screw-body part 41 of screw device 40a can be normal threads with equal thread pitch. In FIG. 18B, the screw device 40b is almost identical to the screw devices 40a of FIG. 18A, only that both first and second mating structures 432b, 422b are threaded.

Figure 19:
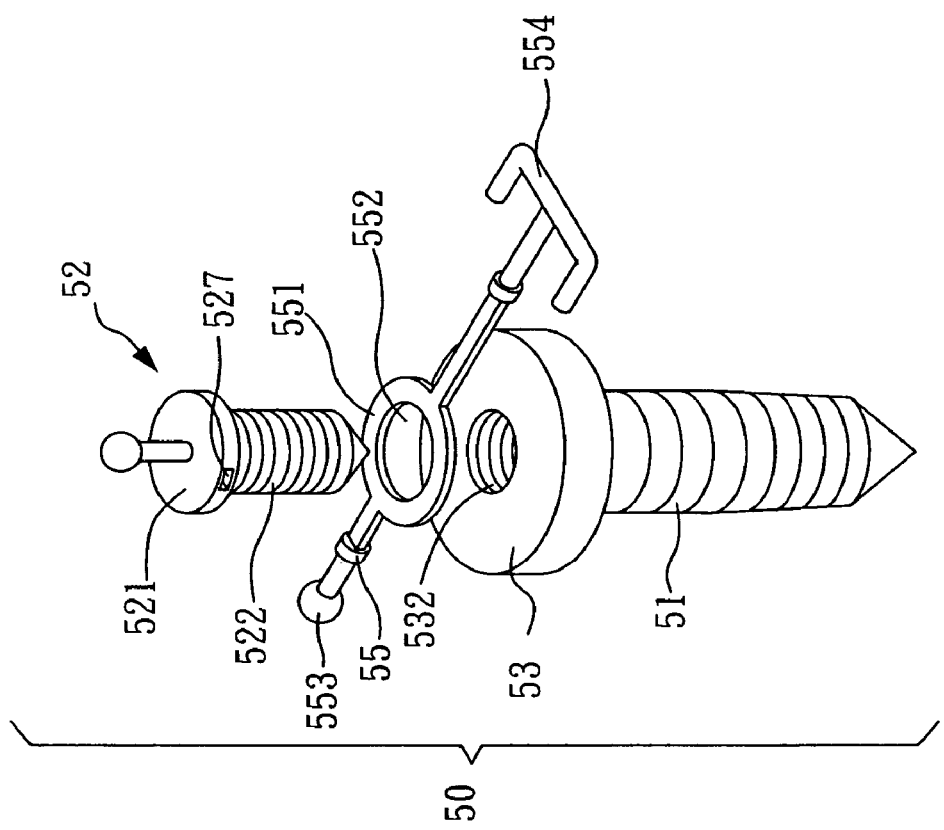
FIG. 19 is the fourteenth preferred embodiment of the screw device 50 of the present invention.

Please refer to FIG. 19, which is the fourteenth preferred embodiment of the screw device 50 of the present invention. Because the screw device 50 shown in FIG. 19 is similar to the screw device 60 shown in FIG. 2, therefore, only the differences will be illustrated herein. In FIG. 19, in addition to the screw-body part 51, head part 52 and platform part 53 which are the fundamental components that can be seen in all embodiments of the present invention, the screw device 50 of the fourteenth preferred embodiment further comprises an additional auxiliary unit 55 which can be firmly clamped between the head part 52 and platform part 53 when the second mating structure 522 is mated with the first mating structure 532. The auxiliary unit 55 comprises a hollow ring portion 551 having a center hole 552, a first accessory member 553 and a second accessory member 554. The hollow ring portion 551 is made of thin metal plate having at least two bendable connecting arms for connecting the first accessory member 553 and a second accessory member 554 respectively. The size of the center hole 552 is smaller than the flat cap 521 of head part 52. Such that, when the second mating structure 522 passes through the center hole 552 and mates with the first mating structure 532, the ring portion 551 will be clamped between the flat cap 521 and platform part 53. In this preferred embodiment, the first accessory member 553 is a rod-type structure having a ball end, while the second accessory member 554 is an E-shaped structure having two L-shaped hooks located at two ends for hooking orthodontic springs. Because the connecting arms of the hollow ring portion 551 are made of thing metal plate and are bendable, angles of the first and second accessory members 553, 554 can be easily adjusted. In addition, the flat cap 521 of head part 52 can be further formed with a rectangular through hole 527 for allowing an orthodontic archwire to pass through.

Figure 20:
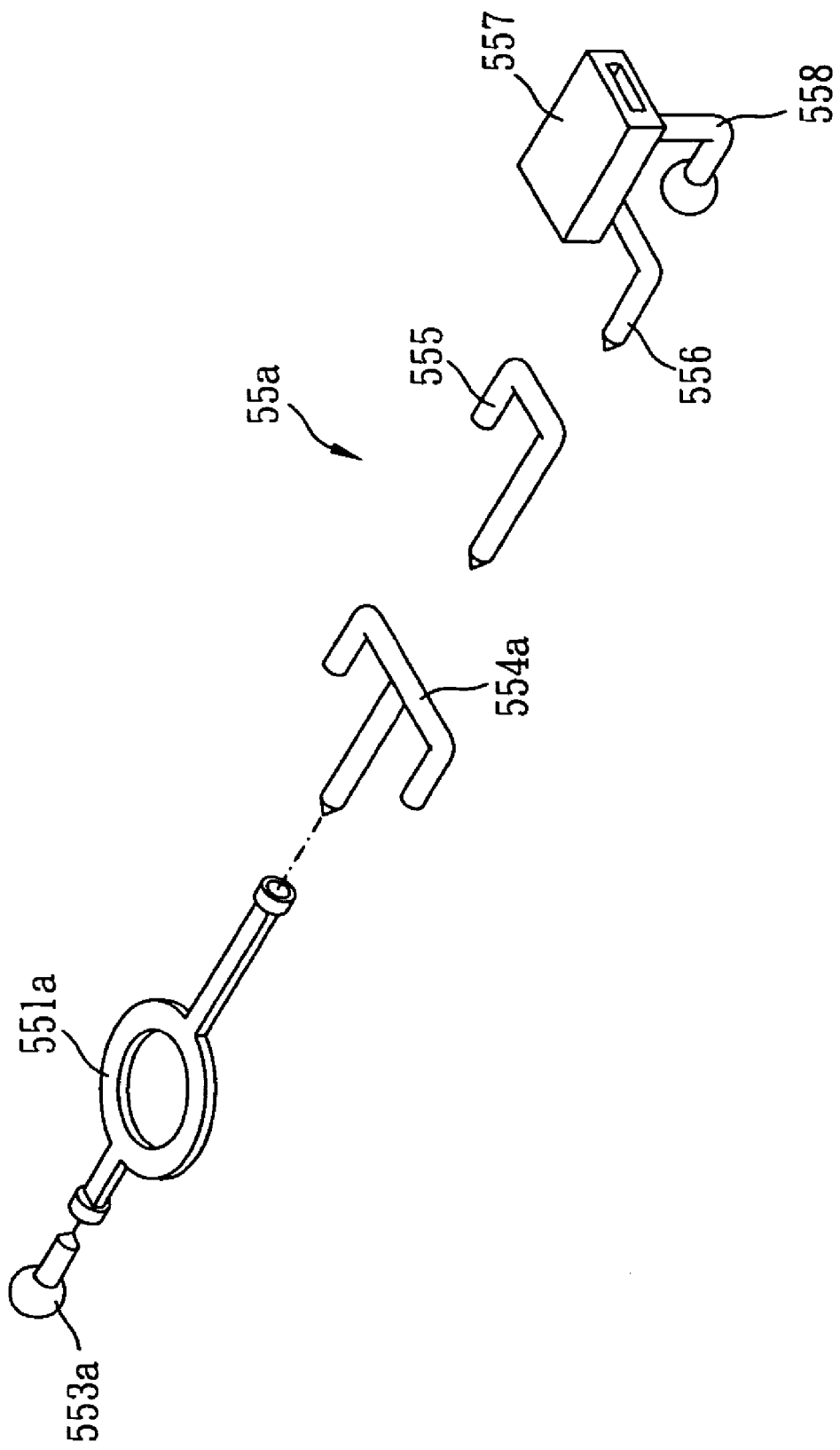

Preferably, the first and second accessory members 553, 554 can be detachable from the ring portion 551 of auxiliary unit 55. Please refer to FIG. 20, which shows the embodiment that the first and second accessory members 553a, 554a are detachable from the flat and bendable ring portion 551a of auxiliary unit 55a. The first and second accessory members 553a, 554a can be selectively attached to the ring portion 551a by means of flanges, adhesive, threads or welding. Such that, the accessory members 553a, 554a can be easily replaced by the fourth accessory member 555 of L-shaped or the fifth accessory member 556 which is further furnished with a rectangular tube 557 and a hook 558 thereon. The rectangular tube 557 is capable of receiving an orthodontic lever arm (not shown in figures), while the hook 558 can be used to hook an orthodontic spring.

Figure 21:
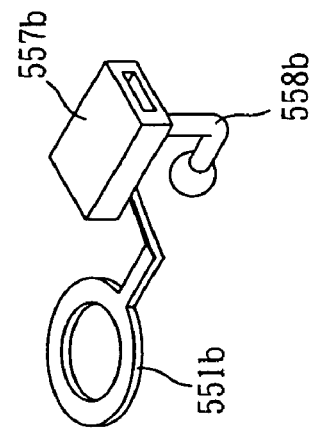
FIG. 21 shows an embodiment that the rectangular tube 557b is fixed to the ring portion 551b in an undetachable manner.

In yet another preferred embodiment shown in FIG. 21, the rectangular tube 557b together with the hook 558b can also be fixed to the ring portion 551b in an undetachable manner.

Although the present invention has been described with reference to a preferred embodiment, it should be appreciated that various modifications and adaptations can be made without departing from the scope of the invention as defined in the claims.

What is claimed is:

1. A screw device for orthodontic treatment comprising:
a screw-body part having a diameter with external threads extending a length;
a platform part axially aligned and integrally formed with the screw-body part, the platform part further having:
a top plane perpendicular to the screw-body part; and
an outer periphery being a smooth surface without threads thereon; and
a head part connected on the flat top plane to the platform part;

wherein, the threads of the screw-body part are divided into at least a first thread portion located near to the platform part and a second thread portion located away from the platform part, the threads of the first thread portion are designed to have relatively narrower width and smaller pitch, while the threads of the second thread portion have wider width and larger pitch;

wherein, the screw device further comprises an auxiliary unit located between the head part and the platform part, the auxiliary unit has a hollow ring portion having a center hole and at least one accessory member for assisting orthodontic treatment, wherein a concave is formed downward from a bottom side of the head part.

2. The screw device for orthodontic treatment according to claim 1, wherein the head part is detachable from the platform part.

3. The screw device for orthodontic treatment according to claim 2, wherein the ring portion of auxiliary unit is clamped between the head part and the platform part and is detachable when the head part is detached from the platform part.

4. The screw device for orthodontic treatment according to claim 1, wherein the screw-body part is tapered at a section away from the platform part, and said tapered section of the screw-body part has a tapering angle of 2–10 degrees.

5. The screw device for orthodontic treatment according to claim 1, wherein the head part further comprises a neck portion having a diameter smaller than which of the platform part, in addition, a rectangular through hole is formed on the neck portion.

6. The screw device for orthodontic treatment according to claim 1, wherein the screw-body part is tapered and includes a no-thread section near to the platform part, a rectangular through hole is formed in the platform part for allowing an orthodontic archwire to pass therethrough.

7. The screw device for orthodontic treatment according to claim 1, wherein some of the external threads of the screw-body part are painted with different colors; these color-painted threads are spaced apart from each other with predetermined distance so as to act like scales to indicate how deep this screw device is fastened.

8. A screw device for orthodontic treatment comprising:
a screw-body part having a diameter with external threads extending a length;
a platform part axially aligned and integrally formed with the screw-body part, the platform part further having:
a top plane perpendicular to the screw-body part; and
an outer periphery being a smooth surface without threads thereon; and
a head part connected on the flat top plane to the platform part;
wherein, the head part is detachable from the platform part;
wherein, the screw device further comprises an auxiliary unit located between the head part and the platform part, the auxiliary unit has a hollow ring portion having a center hole and at least one accessory member for assisting orthodontic treatment;
wherein, the ring portion of auxiliary unit is clamped between the head part and the platform part and is detachable when the head part is detached from the platform part,
wherein some of the external threads of the screw-body part are painted with different colors; these color-painted threads are space apart from each other with predetermined distance so as to act like scales to indicate how deep this screw device is fastened.

9. A screw device for orthodontic treatment comprising:
a screw-body part having a diameter with external threads extending a length;
a platform part axially aligned and integrally formed with the screw-body part, the platform part further having:
a top plane perpendicular to the screw-body part; and
an outer periphery being a smooth surface without threads thereon; and
a head part connected on the flat top plane to the platform part;
wherein, the threads of the screw-body part are divided into at least a first thread portion located near to the platform part and a second thread portion located away from the platform part, the threads of the first thread portion are designed to have relatively narrower width and smaller pitch, while the threads of the second thread portion have wider width and larger pitch;
wherein, the screw device further comprises an auxiliary unit located between the head part and the platform part, the auxiliary unit has a hollow ring portion having a center hole and at least one accessory member for assisting orthodontic treatment,
wherein some of the external threads of the screw-body part are painted with different colors; these color-painted threads are spaced apart from each other with predetermined distance so as to act like scales to indicate how deep this screw device is fastened.

* * * * *